(12) United States Patent
Heng

(10) Patent No.: US 7,556,818 B1
(45) Date of Patent: Jul. 7, 2009

(54) COMPOSITION FOR AND METHOD OF TREATING PSORIASIS

(76) Inventor: Madalene C. Y. Heng, 17632 Vincennes St., Northridge, CA (US) 91325

( * ) Notice: Subject to any disclaimer, the term of this patent is extended or adjusted under 35 U.S.C. 154(b) by 1063 days.

(21) Appl. No.: 10/884,231

(22) Filed: Jul. 3, 2004

Related U.S. Application Data

(63) Continuation-in-part of application No. 10/434,006, filed on May 7, 2003, now abandoned.

(51) Int. Cl.
*A61F 9/00* (2006.01)
*A61K 36/886* (2006.01)

(52) U.S. Cl. ............... 424/400; 424/744; 514/863; 514/886; 514/944; 514/969

(58) Field of Classification Search ........... 514/680, 514/863, 886, 944, 969; 424/400, 744
See application file for complete search history.

(56) References Cited

U.S. PATENT DOCUMENTS

2001/0051184 A1* 12/2001 Heng ................... 424/461

* cited by examiner

*Primary Examiner*—Sreeni Padmanabhan
*Assistant Examiner*—Umamaheswari Ramachandran
(74) *Attorney, Agent, or Firm*—Jack Munro; Sandy Lipkin

(57) ABSTRACT

A composition and method of applying to skin which has psoriasis a gel that contains curcumin and/or curcuminoids. Prior to applying of the gel to the skin, the affected layer is soaked in one-hundred percent alcohol. The alcohol functions to dissolve the curcumin and/or curcuminoids with the alcohol not only comprising a solvent but functions as a carrier to cause the freshly dissolved (nascent) curcumin to penetrate through the stratum corneum layer of the skin and into the epithelial layer of the skin.

4 Claims, No Drawings

COMPOSITION FOR AND METHOD OF TREATING PSORIASIS

REFERENCE TO PRIOR APPLICATION

This application is a continuation-in-part of U.S. patent application Ser. No. 10/434,006, filed May 7, 2003 now abandoned, by the same title and same inventor.

BACKGROUND OF THE INVENTION

1. Field of the Invention

The field of this invention relates to a gel liquid composition for treating of psoriasis and also to the method of applying the composition to achieve effective penetration of the healing agent contained within the gel liquid.

2. Description of the Related Art

Psoriasis is an inflammatory skin disease of unknown cause which is usually chronic, frequently recurrent and acute in nature. This skin disease produces lesions that occur predominantly at certain sites, such as elbows, knees and scalp although other areas of the body may be also inflamed. Psoriasis consists of dull red, well defined patches usually covered by distinctive silvery scales which, when removed, disclose tiny capillary bleeding points. These lesions spread by peripheral extension and may involve huge areas of the body. The patches are not constant in size, shape and location. It is believed that the psoriasis is activated by external stimuli, such as trauma or bacteria, which trigger the psoriatic process in genetically predisposed individuals.

Compartmentalized epidermal T cells in psoriatic skin are thought to release cytokines that induce the psoriatic keratinocyte phenotype, which is associated with epidermal growth factor (EGF)-dependent proliferation. EGF dependent proliferation is stimulated by phosphorylation of its receptor, tyrosine kinase, which is dependent on the activity of phosphorylase kinase (PhK). PhK is also known as adenosine triphosphate (ATP)-phosphorylase b phosphotransferase. PhK is a multimeric enzyme. This enzyme was thought to function mainly in coupling muscle contraction with energy production. It also functions in cell motility and cell proliferation. PhK activity appears to be elevated in psoriasis resulting in an increase in glycogenolysis, phosphorylation reactions and psoriatic activity. It is believed that the persistence of high levels of PhK contributes to the chronicity of the psoriatic patches.

SUMMARY OF THE INVENTION

A method of inhibiting proliferation of psoriatic epidermal cells within an affected area that comprises the steps of soaking the affected area with an alcohol and then applying onto the alcohol layer a layer of curcumin dispersed in the gel where the alcohol dissolves the curcumin and functions not only as a solvent but also as a carrier for the curcumin and/or curcuminoids in order to penetrate through the different layers of the skin.

A further embodiment of the present invention is where the method of this invention is modified by utilizing of 0.001 percent to ten percent by volume of curcumin and/or curcuminoids (derivatives of curcumin) within the gel.

A further embodiment of the present invention is where the method of this invention is modified by the alcohol being selected from the group of isopropyl, ethyl, propyl, butyl, methyl and isobutyl.

A further embodiment of the present invention is where the method of this invention is modified by the applying step being accomplished by kneading the gel within the alcohol layer.

DETAILED DESCRIPTION OF THE INVENTION

Psoriasis is an exceedingly undesirable skin disease. The skin becomes thickened with discolored plaques producing scales. Not only is it exceedingly ugly in appearance, it is painful to the patient and any contact, such as scratching, will result in bleeding.

Prior to the present invention, there has been no known cure for psoriasis. The treatments that have been applied might improve the psoriasis for a period of time but, in almost all cases, will recur. The subject invention provides for a composition that is to be applied to the psoriatic skin where the psoriasis is not only diminished but can actually be eliminated.

Reference is to be had to U.S. Pat. No. 5,925,376, by the present inventor, which discusses the applying of curcumin onto psoriatic skin. The curcumin affects the activity of PhK and reduces the activity of PhK. Decreasing the PhK decreases the psoriasis, and if the PhK can be lowered sufficiently, completely eliminate the psoriasis thereby curing the patient of the disease.

It was to be found to be desirable in U.S. Pat. No. 5,925,376 to put the curcumin within an aqueous solution. The aqueous solution could contain an alcohol. The curcumin, in patent '376, is advocated to be used orally. Curcumin is a major active component of the food flavor tumeric. It has been found that curcumin is a selective inhibitor of phosphorylase kinase. In addition, curcumin inhibits tumor promotion caused by phorbolesters. Patent No. '376 also discusses including of curcumin within a gel, such as an aloe vera gel.

The subject invention has discovered an improvement over patent No. '376. Curcumin is readily dissolvable in alcohol. Alcohol easily penetrates skin, and not only penetrates the outer layer (stratum corneum) layer of the skin but also seeps into and penetrates the inner layer (epithelial layer) of the skin.

It has been discovered that substantially increased penetration by the curcumin and/or curcuminoids, two examples of which are demethylcurcumin, bisdemethylcurcumin, can be achieved by first applying to the skin a one-hundred percent alcohol layer. No minor amount of alcohol is applied. The affected area is soaked as much as possible with the alcohol. The alcohol provides the solvent and the carrier for the curcumin. The alcohol, thus applied, allows curcumin to be freshly dissolved on the skin, thus producing a nascent condition in conjunction with the curcumin. Application of a curcumin composition onto the alcohol layer on the skin results in the curcumin freshly dissolving (i.e. nascent) within the alcohol. The curcumin in this nascent state of solution in alcohol has better penetrating properties and is thus carried by the alcohol deep within the skin to treat the psoriasis at its core. It has been observed that at the movement of curcumin dissolving into the alcohol (i.e. nascent state), there is an increased ability of the curcumin-alcohol solution to penetrate into the deeper layers of the skin.

The preferable application comprises applying of a generous quantity of the alcohol directly onto the skin covering the skin well over the psoriasis; then immediately applying to the alcohol layer on the skin before it has a chance to evaporate a gel, such as an aloe vera gel within which is contained between 0.001 percent to ten percent by volume of curcumin. A typical alcohol can be any one selected from the group consisting of isopropyl, ethyl, propyl, butyl, methyl and isobutyl. The preferable technique for applying of the gel to the alcohol layer is by kneading. Kneading comprises physically massaging the curcumin containing gel in conjunction with the alcohol for a short period of time, such as a few minutes. After that period of time, the psoriatic skin will appear as it did before the treatment. Treatments are to occur on a daily basis or a few times a week over a length of time sufficient to completely cure the patient of the psoriasis. As the skin is treated, the skin will gradually improve as the weeks go by. Typical treatment times would be from six weeks to three months for a complete cure.

Staining of the stratum corneum is an indication of the amount of curcumin at the skin's surface. For 0.25 percent amount of curcumin, the color will be light yellow. A 0.5 percent curcumin will show an intermediate yellow. A one percent curcumin will show a dark yellow color. This will give a visual reflection of the amount of transference of the curcumin from the gel to the stratum corneum. The color of the skin will assist the medical practitioner in making a judgment regarding using the correct quantity of curcumin for the specific patient. Typically, the gel can include any desirable base. Aloe vera is one such desirable base.

What is claimed is:

1. A method of inhibiting proliferation of psoriatic epidermal cells within an affected area comprising the steps of:

utilizing of curcumin and/or curcuminoids dispersed in a gel by immediately applying said gel to the affected area that has been pre-treated by first soaking the affected area with an alcohol solution to inhibit the proliferation of psoriatic epidermal cells within an affected area so that said alcohol can freshly dissolve the (nascent) curcumin and/or circuminoids functioning as a solvent and a carrier for the curcumin to penetrate the skin with the penetration not only occurring within the stratum corneum layer of the skin but also in the epithelial layer of the skin.

2. The method as defined in claim 1 where the amount of curcumin dispersed in said gel is within the range of 0.001 percent to ten percent by volume of said gel.

3. The method as defined in claim 1 wherein the alcohol is within the group consisting of isopropyl, ethyl, propyl, buytl, methyl and isobutyl.

4. The method as defined in claim 1 wherein the step of pre-treating the affected area is accomplished through the kneading said gel within said alcohol layer.

* * * * *